United States Patent [19]

Wuest et al.

[11] Patent Number: 5,326,900
[45] Date of Patent: Jul. 5, 1994

[54] AROMATIC KETO COMPOUNDS, THE PREPARATION THEREOF, AND DRUGS AND COSMETICS CONTAINING THESE

[75] Inventors: Hans-Heiner Wuest, Dossenheim; Bernd Janssen, Ludwigshafen, both of Fed. Rep. of Germany

[73] Assignee: BASF Aktiengesellschaft, Ludwigshafen, Fed. Rep. of Germany

[21] Appl. No.: 985,927

[22] Filed: Dec. 4, 1992

Related U.S. Application Data

[62] Division of Ser. No. 790,452, Nov. 12, 1991, Pat. No. 5,194,664, which is a division of Ser. No. 467,193, Jan. 18, 1990, abandoned.

[30] Foreign Application Priority Data

Feb. 10, 1989 [DE] Fed. Rep. of Germany ....... 3903992

[51] Int. Cl.$^5$ .............................................. C07C 69/76
[52] U.S. Cl. ........................................ 560/51; 560/53; 558/61; 568/28; 568/37
[58] Field of Search ............... 560/51, 53; 558/61; 568/28, 37; 514/532, 545, 600

[56] References Cited

U.S. PATENT DOCUMENTS

| | | | |
|---|---|---|---|
| 4,326,055 | 4/1982 | Loeliger | 560/51 |
| 4,831,052 | 5/1989 | Shudo | 514/455 |
| 4,833,240 | 5/1989 | Maignan et al. | 560/51 |

FOREIGN PATENT DOCUMENTS

| | | |
|---|---|---|
| 1183541 | 3/1985 | Canada . |
| 3531722 | 3/1986 | Fed. Rep. of Germany . |
| 3903992 | 8/1990 | Fed. Rep. of Germany . |

OTHER PUBLICATIONS

Lindamood, C. et al., Fundam. Appl. Toxicol., 8(4), 517-30, 1987.
Lindamood, C. III et al., Fundam. Appl. Toxicol., 14(1), 15-29, 1990.
Krailler, R. E. et al., J. Liq. Chromatogr., 14(12), 2383-98, 1991.
Kagedrika, L. et al., J. Med. Chem. 32(5), 1095-1205, 1989.

Primary Examiner—Paul J. Killos
Attorney, Agent, or Firm—Oblon, Spivak, McClelland, Maier & Neustadt

[57] ABSTRACT

Compounds of the general formula I

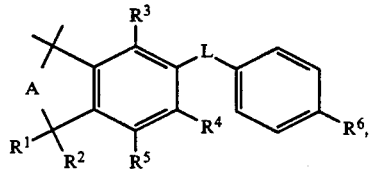

and drugs and cosmetics prepared therefrom are described.

11 Claims, No Drawings

AROMATIC KETO COMPOUNDS, THE PREPARATION THEREOF, AND DRUGS AND COSMETICS CONTAINING THESE

This is a division of application Ser. No. 07/790,452, filed on Nov. 12, 1991, U.S. Pat. No. 5,194,664 which is a divisional application of Ser. No. 07/467,193 filed Jan. 18, 1990, now abandoned.

The present invention relates to novel aromatic keto compounds, to processes for the preparation thereof and to agents prepared therefrom for controlling and preventing diseases.

U.S. Pat. No. 4,326,055 and CA 1,183,54 1 disclose the pharmacological effects of retinoidal benzoic acid derivatives on topical and systemic therapy of neoplasms and dermatoses, e.g. ache or psoriasis. The disadvantage of these compounds is that they have a low therapeutic index because of the side effects comprised by the term hypervitaminosis A.

We have now found that compounds of the general formula I

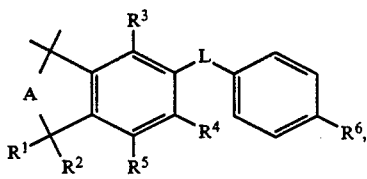

where

A is ethylene or methylene which can be substituted by methyl, hydroxyl or oxo, L is one of the following

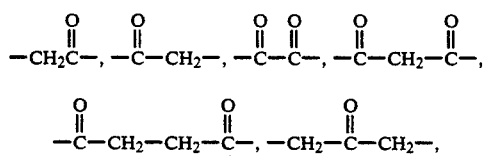

$R^1$ and $R^2$ are hydrogen or methyl,
$R^3$ is hydrogen, hydroxyl or $C_1$-$C_6$-alkoxy,
$R^4$ is hydrogen, $C_1$-$C_4$-alkyl, halogen or methoxy,
$R^5$ is hydrogen or methoxy, and
$R^6$ is hydrogen, methyl, cyano, a $C_2$-$C_{10}$ group of the formula

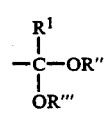

where R', R" and R'" are each alkyl of 1 to 9 carbons, the total of carbons in R', R", R'" is 2 to 10, and R' can also be hydrogen, or the following

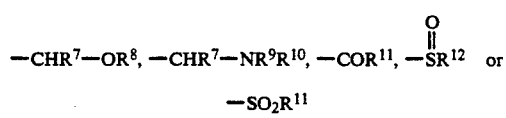

where
$R^7$ is hydrogen or $C_1$-$C_4$-alkyl, $R^8$ is hydrogen, $C_1$-$C_4$-alkyl, $C_1$-$C_{20}$-alkanoyl, or benzoyl which can be substituted,
$R^9$ and $R^{10}$ are hydrogen, $C_1$-$C_4$-alkyl, $C_1$-$C_6$-alkanoyl, or benzoyl which can be substituted, or form, together with the nitrogen to which they are bonded, a 5- or 6-membered saturated heterocyclic radical which can also contain an oxygen in addition to the nitrogen,
$R^{11}$ is hydrogen, $C_1$-$C_4$-alkyl or $-OR^{13}$ or $-NR^{14}R^{15}$ where $R^{13}$ is hydrogen, $C_1$-$C_8$-alkyl which can be substituted by 1 or 2 hydroxyls, or aryl or aralkyl each of which can be substituted in the aryl moiety, and where $R^{14}$ and $R^{15}$ are hydrogen, or aralkyl or aryl which can be substituted, or $R^{14}$ and $R^{15}$ form, together with the nitrogen to which they are bonded, a 5- or 6-membered saturated heterocyclic radical which can also contain an oxygen in addition to the nitrogen, and
$R^{12}$ is $C_1$-$C_4$-alkyl, and the physiologically tolerated salts thereof have an improved profile of action, in particular with regard to side effects.

Particularly suitable heterocyclic radicals $-NR^9R^{10}$ and $-NR^{14}R^{15}$ are pyrrolidinyl, piperidinyl and morpholinyl. Preferred substituents on the benzoyl ($R^8$, $R^9$ and $R^{10}$) are methoxy, nitro, methyl or halogen, especially chlorine or bromine. The preferred aryl ($R^{13}, R^{14}, R^{15}$) is phenyl which can be substituted by methyl, methoxy or cyano. The preferred aralkyl ($R^{13}, R^{14}, R^{15}$) is benzyl, which can be substituted in the aryl moiety by, in particular, methyl, methoxy or halogen, preferably chlorine or bromine.

The preferred halogen for $R^4$ is fluorine.

The compounds of the formula I according to the invention can be prepared by conventional processes. A review of the various methods for preparing ketones is to be found in "Methoden der Organischen Chemie" (Houben-Weyl-Müller), Volume 7/2a-c, Georg Thieme Verlag Stuttgart.

The methods mainly used for synthesizing the compounds according to the invention are described hereinafters:

1. Deoxybenzoins of the formula I (L=—CH₂—CO— or —CO—CH₂—) can be obtained, for example, by
   a) reacting a phosphonic ester of the formula II

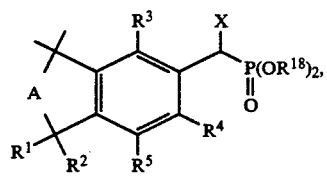

where A and $R^1$—$R^5$ have the abovementioned meanings, and X is $-OR^{16}$ or $-NR^{16}R^{17}$ where $R^{16}$ and $R^{17}$ are $C_1$-$C_4$-alkyl, it being possible for $R^3$ and $R^{16}$ together to form a $C_1$-$C_3$-alkylene chain, and $R^{18}$ is $C_1$-$C_4$-alkyl, with an aldehyde of the formula III

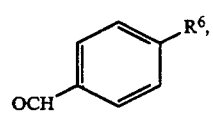

where $R^6$ has the abovementioned meaning, in the presence of a base in a Wittig-Horner reaction, and subjecting the resulting enamine ($X=NR^{16}R^{17}$) or enol ether ($X=OR^{16}$) to acid hydrolysis, or by b) reacting a carbonyl chloride of the formula IV or V

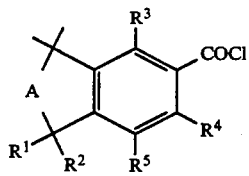

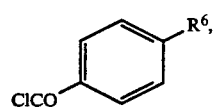

where A and $R^1$—$R^6$ have the abovementioned meanings, with a benzyl halide of the formula VI or VII

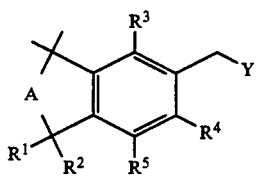

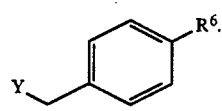

where A and $R^1$—$R^6$ have the abovementioned meanings, and Y is chlorine or bromine, in the presence of a suitable metal, with or without the addition of catalytic amounts of a transition metal catalyst, the reaction being between either IV and VII or V and VI.

2. 1,3-diketo compounds of the formula I according to the invention, with $L=$—$C(O)CH_2C(O)$— or the tautomeric enol compounds, can be prepared, for example, by a) reacting a ketone of the formula VIII

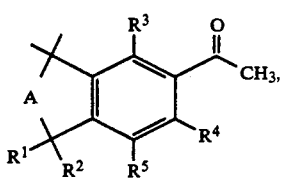

where A and $R^1$—$R^5$ have the abovementioned meanings, with a terephthalic ester of the formula IX

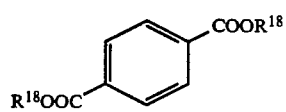

where $R^{18}$ is $C_1$-$C_4$-alkyl, in the presence of a base, or by b) subjecting a chalcone of the formula X

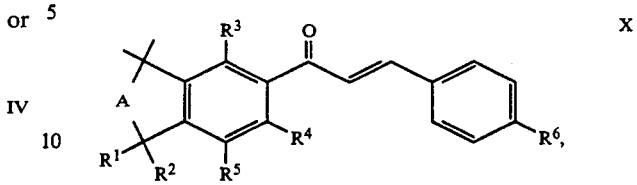

where A and $R^1$—$R^6$ have the abovementioned meanings, to addition of bromine, then eliminating hydrogen bromide with a suitable base, and finally carrying out acid hydrolysis.

3. The 1,4-diketo compounds of the formula I according to the invention ($L=$—$C(O)CH_2CH_2C(O)$—) can be prepared by reacting a chloroethyl ketone of the formula XI,

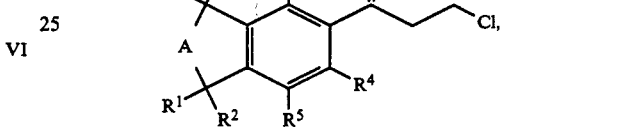

where A and $R^1$—$R^5$ have the abovementioned meanings, with a suitable base to give a vinyl ketone of the formula XII

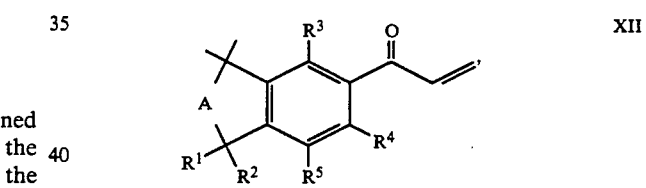

where A and $R^1$—$R^5$ have the abovementioned meanings, and then reacting the latter with a benzaldehyde of the formula XIII

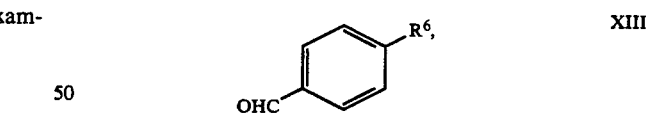

where $R^6$ has the abovementioned meaning, in the presence of an "umpolung" catalyst (see, for example, H. Stetter, and J. Krasselt, J. Heterocyclic Chem. 14, 573 (1977).

4. It is also possible to convert the compounds of the formula I which have been prepared by the processes described under 1.—3. or by other processes into other compounds of the formula I according to the invention by modifying the radical $R^6$.

The Wittig-Horner reaction in 1.a) is carried out in the solvents conventional for this purpose, such as tetrahydrofuran, diethy 1 ether, 1,2-dimethoxyethane, n-hexane, petroleum ether, toluene, dimethyl sulfoxide, dimethylformamide or mixtures thereof at from −78° to 60° C., the temperature being greatly dependent on the base which is employed.

The bases which are used are sodium hydride, the sodium salt of dimethyl sulfoxide, alcoholates such as sodium methanolate or potassium tert-butanolate, or organolithiums such as n-butyllithium. Preferably used for the metalation of the phosphonic esters of the formula II is n-butyllithium at from $-78°$ to $-60°$ C., and this is followed by addition of the benzaldehyde and allowing the reaction to go to completion at up to 25° C.

The reaction in 1.b) requires at least equimolar amounts of a metal and/or metal salt. Produced as intermediates are the corresponding organometallic compounds, e.g. of magnesium, cadmium, zinc or lithium. Zinc is particularly advantageous, preferably zinc which has previously been activated with copper or silver. Catalytic amounts of a transition metal catalyst can be added, preferably containing palladium or nickel, e.g. bis(triphenylphosphine)palladium(II) chloride or tetrakis (triphenylphosphine)palladium. It is particularly beneficial to add such catalysts when zinc is used as reductive metal.

Mainly used as solvents are ethers such as diethyl ether, tetrahydrofuran, dioxane or 1,2-dimethoxyethane, and possibly also aromatic hydrocarbons such as benzene or toluene. The reactions are carried out at from 0° to 60° C., preferably at 20°–40° C.

Ester condensations as in 2.a) can in principle take place with either basic or acid catalysis, but bases are mostly used, e.g. alkali metal hydrides such as sodium hydride, alkali metal alcoholates such as sodium methanolate or potassium tert-butanolate, or alkali metalamides such as those of lithium, sodium or potassium.

Solvents which are expediently used are alcohols such as methanol or ethanol, ethers such as diethyl ether, diisopropyl ether, tetrahydrofuran, dioxane or 1,2-dimethoxyethane, aromatic hydrocarbons such as toluene or xylene, or else dimethylformamide. The reactions are carried out at from 20° to 140° C., preferably from 80° to 120° C.

Examples of suitable bases in 2.b) are alcoholates such as sodium methanolate or potassium tertbutanolate. The hydrolysis is brought about with dilute or concentrated mineral acids such as hydrochloric acid or sulfuric acid.

Suitable for the elimination of hydrogen chloride in 3. are, in particular, organic nitrogen bases such as triethylamine or pyridine. The vinyl ketones of the formula XII can be isolated, but further reaction in situ is beneficial. The coupling with the benzaldehyde derivative of the formula XIII in an umpolung reaction is catalyzed by cyanide ions or, even better, by thiazolium salts such as 3-benzyl-5-(2-hydroxyethyl)-4-methylthiazolium-chloride. Dimethylformamide is preferably used as solvent.

Examples of methods 4. are:

Benzoic esters or benzonitriles of the general formula I where $R^6$ is carboalkoxy or cyano can be converted into the free carboxylic acids and the physiologically tolerated salts thereof by hydrolysis. The hydrolysis is preferably carried out in a mixture of a lower aliphatic alcohol such as methanol, ethanol, propanol, isopropanol or n-butanol with water in the presence of an excess of an alkali metal hydroxide, preferably sodium or potassium hydroxide, at the boiling point of the reaction mixture.

The amides according to the invention can be prepared in a conventional manner by converting the corresponding benzoic acids into more active derivatives, e.g. into the carbonyl halides, azides, imidazolides or anhydrides, and treating the latter with amines $HNR^{14}R^{15}$.

A carboxylic acid or ester or amide thereof or a nitrile of the formula I can be reduced in a conventional manner to the corresponding alcohols or amines. The reaction is advantageously carried out with a metal hydride or alkali metal hydride in the presence of a suitable solvent. The metal hydrides which are preferably employed are complex metal hydrides such as lithium aluminum hydride or lithium borohydride or diisobutyl aluminum hydride. Preferred solvents are ethers such as diethyl ether, tetrahydrofuran, dioxane or 1,2-dimethoxyethane.

An alcohol or amine of the formula I can be acylated in a conventional manner with alkanoyl or aroyl chloride or anhydride to give the corresponding ester or amide, or alkylated with an alkyl halide, preferably an alkyl bromide or iodide, to give the corresponding ether or more highly alkylated amine, or oxidized with suitable oxidizing agents such as manganese(IV) oxide to give the corresponding aldehyde.

An aldehyde of the formula I can also be obtained by reducing the corresponding nitrile of the formula I with diisobutylaluminum hydride in a solvent, preferably toluene, hexane or tetrahydrofuran, at from $-40°$ C. to room temperature.

The compounds according to the invention and their physiologically tolerated salts can, by reason of their pharmacological properties, be used for the topical and systemic therapy and prophylaxis of precanceroses and carcinomas of the skin, the mucous membranes and internal organs and for the topical and systemic therapy of acne, psoriasis and other dermatological disorders associated with pathological keratinization, especially ichthyosis, Darier's disease, herpes and leukoplakia but also eczema, vitiligo, warts, phototoxis (premature ageing) of the skin, and dry eyes and other corneopathies and for the treatment of rheumatic disorders, especially those of an inflammatory or degenerative nature and which affect Joints, muscles, tendons and other parts of the locomotor system. Preferred indications are: the therapy of dermatological disorders, of skin damage caused by sunlight, and of iatrogenic skin damage, e.g. atrophy induced by corticosteroids, and the prophylactic treatment of precanceroses and tumors.

The pharmacological effects can be shown, for example, in the following tests: the compounds according to the invention abolish the keratinization which starts in hamster tracheal tissue in vitro after vitamin A deficiency. The keratinization is part of the early phase of carcinogenesis, which is inhibited by the compounds of the formula I according to the invention in a similar test in vivo after initiation by chemical compounds, by energetic radiation or after vital cell transformation. These methods are described in Cancer Res. 36 (1972) 964–972 and Nature 250 (1974) 64–66 and 253, (1975) 47–50.

In addition, the compounds according to the invention inhibit the proliferation of certain malignant cells. This method is described in J. Natl. Cancer Inst. 60 (1978) 1035–1041, Experimental Cell Research 117 (1978) 15–22 and Proc. Natl. Acad. Sci. USA 77 (1980) 2937–2940.

The antiarthritic effect of the compounds according to the invention can be determined in a conventional manner in animal experiments using the adjuvant arthritis or streptococci cell wall induced arthritis model. The dermatological activity, for example for the treatment of ache, can be demonstrated, inter alia, by the comedolytic activity and the ability to reduce the number of cysts in the rhino mouse model.

The latter method is described by L. H. Kligman et al. in the Journal of Investigative Dermatology 73 (1978) 354–358.

The dermatological activity can also be measured by the reduction in sebaceous glands and the associated diminution in sebum production by the flank organ of the hamerst. This method is described by E. C. Gomez in J. Am. Dermatol. 6 (1982) 746–750.

Furthermore, it is possible to determine the reversal which can be achieved with compounds according to the invention of skin damage caused by UV light in animal models. This method is described by L. H. Kligman et al. in Connect. Tissue Res. 12, (1984) 139–150 and in the Journal of the American Academy of Dermatology 15 (1986) 779–785.

Accordingly, the invention furthermore relates to therapeutic agents for topical and systemic administration and to cosmetic agents which contain a compound of the formula I as active substance in addition to conventional carriers or diluents.

The agents can accordingly be administered orally, parenterally or topically. Examples of suitable formulations are uncoated or ( film-coated tablets, capsules, pills, powders, solutions or suspensions, infusion or injection solutions and pastes, ointments, gels, creams, lotions, dusting powders, solutions or emulsions and sprays.

The therapeutic or cosmetic agents can contain the compounds to be used according to the invention in a concentration of 0.0001 to 1%, preferably 0.00 1 to 0.1%, for local use, and preferably in a single dose of 0.1 to 50 mg for systemic use, and are administered in one or more doses each day depending on the nature and severity of the disorders.

The drugs and cosmetics of the invention are produced in a conventional manner using the conventional solid or liquid carriers or diluents and the auxiliaries which are conventionally used in pharmaceutical technology to accord with the desired mode of administration and with a suitable dosage. Tablets can be obtained, for example, by mixing the active substance with known auxiliaries, for example inert diluents such as dextrose, sugar, sorbitol, mannitol or polyvinylpyrrolidone, disintegrants, such as corn starch or alginic acid, binders such as starch or gelatin, lubricants such as magnesium arearate or talc and/or agents to achieve a depot effect, such as carboxypolymethylene, carboxymethylcellulose, cellulose acetate phthalate or polyvinyl acetate. The tablets can also be composed of several layers.

Appropriate coated tablets can be produced by coating cores, which have been produced in a similar manner to the tablets, with conventional coating agents, for example polyvinylpyrrolidone or shellac, gum arabic, talc, titanium dioxide or sugar. The coating can also be composed of several layers, it being possible to use the auxiliaries mentioned above for tablets.

Solutions or suspensions containing the active substance according to the invention can additionally contain taste corrigents such as saccharin, cyclamate or sugar as well as, for example, flavorings such as vanillin or orange extract. They can moreover contain suspending auxiliaries such as sodium carboxymethylcelhlose or preservatives such as p-hydroxybenzoates. Capsules containing active substances can be produced, for example, by the active substance being mixed with an inert carrier such as lactose or sorbitol and encapsulated in gelatin capsules.

Examples of conventional ingredients of cosmetic and pharmaceutical formulations for topical use ares anionic, cationic and nonionic emulsifiers and emulsion stabilizers which can simultaneously act as bodying agents or gel formers, such as polyvinylpyrrolidone, fatty alcohols, glycerol monostearate, polyacrylic acids, cellulose derivatives and ethylene oxide/propylene oxide block polymers, solid or liquid oily components or fats of mineral, vegetable or animal origin, synthetic oily esters such as glycerol triesters and isopropyl myristate, hydrophilic components such as glycerol, polyethylene glycol and propylene glycol.

Examples of further ingredients of cosmetics are sunscreen agents, suntan agents, preservatives, antioxidants, pigments, colorants, essential oils and perfume oils, vitamins, plant extracts, collagen etc. These substances are described, for example, in the CTFA Cosmetic Ingredient Dictionary, 3rd edition, Washington 1982.

Some of the compounds according to the invention have an acidic hydrogen and can therefore be converted with bases in a conventional manner into a physiologically tolerated salt which is readily soluble in water. Examples of suitable salts are ammonium and alkali metal salts, especially of sodium, potassium and lithium, and alkaline earth metal salts, especially of calcium or magnesium, as well as salts with suitable organic bases, such as $C_1$-$C_6$-alkylamines, e.g. methylamine, ethylamine or cyclohexylamine, or with substituted $C_1C_6$-alkylamines, especially hydroxyl-substituted alkylamines such as diethanolamine, triethanolamine and tris(-hydroxymethyl)aminomethane, and with piperidine or morpholine.

The amines of the formula I according to the invention which have been obtained can be converted by conventional procedures into the acid addition salt of a physiologically tolerated acid. Examples of suitable physiologically tolerated inorganic acids are hydrochloric acid, hydrobromic acid, phosphoric acid or sulfuric acid, and of organic acids are oxalic acid, maleic acid, fumaric acid, lactic acid, tartaric acid, malic acid, citric acid, salicylic acid, adipic acid or benzoic acid. Others can be found in "Fortschritte der Arzneimittelforschung" volume 10, pages 224–225, Birkhauser Verlag, Basle and Stuttgart, 1966.

EXAMPLE 1

1-(4-Carbomethoxyphenyl)-3-(5,6,7, 8-tetrahydro-5,5,8,8,-tetramethyl-2-naphthyl)-1,3-propanedione A solution of 19.4 g (0.1 mol) of dimethyl terephthalate and 23 g (0.1 mol) of 6-acetyl-1,2,3,4-tetrahydro-1,1,4,4-tetramethylnaphthalene in 80 ml of toluene and 20 ml of dimethoxyethane was added dropwise under nitrogen to a suspension of 3.6 g (0.15 mol) of sodium hydride in 21 ml of toluene at 100° C. The mixture was refluxed for 5 h and, after cooling, 50 ml of water were added, and the mixture was acidified with 50% concentrated hydrochloric acid, poured into 500 ml of water and extracted with chloroform. The precipitated product was filtered off with suction, and the chloroform phase was dried over sodium sulfate and concentrated. The residue and crude product were mixed and washed several times with hot methanol. Drying of the crystals resulted in 22.1 g of the title compound of melting point 128° C.

EXAMPLE 2

1-(4-Carbomethoxyphenyl)-3-(2,3-dihydro-1,1,2,3,3-pentamethyl-5-(1H)-indenyl)-1,3-propanedione In a similar manner to Example 1, 18.1 g of the title compound of melting point 120°–125° C. were obtained from 23 g (0.1 mol) of 5-acetyl-2,3-dihydro-1,1,2,3,3-pentamethyl-(1H)-indene and 19.4 g (0.1 mol) of dimethyl terephthalate.

EXAMPLE 3

1-(4-Carbomethoxyphenyl)-3-(5,6,7,8-tetrahydro-3,8,8-trimethyl-2-naphthyl)-1,3-propanedione In a similar manner to Example 1, 4.8 g of the title compound of melting point 91°–92° C. were obtained from 10 g (46 mmol) of 7-acetyl-1,2,3, 4-tetrahydro-1,1,6-trimethylnaphthalene and 9 g (46 mmol) of dimethyl terephthalate.

EXAMPLE 4

1-(4-Carboxyphenyl)-3-(5,6,7,8-tetrahydro-5,5,8,8-tetramethyl-2-naphthyl)-1,3-propanedione 20 g (87 mmol) of 6-acetyl-1,2,3, 4-tetrahydro-1,1,4,4-tetramethylnaphthalene, 13 g (87 mmol) of 4-formylbenzoic acid and 8 g of sodium hydroxide pellets were stirred in 100 ml of methanol at room temperature overnight. The mixture was then poured into ice/water and extracted with ether. Remaining ether in the aqueous phase was removed by blowing nitrogen through. It was acidified with concentrated hydrochloric acid, the crystalline precipitate was filtered off with suction, and drying resulted in 24.9 g of 3-(4-carboxyphenyl)-1-(5,6,7,8-tetrahydro-5,5,8,8-tetramethyl-2-naphthyl)-2-propen-1-one of melting point 199°–201° C.

A solution of 8.5 g (53 mmol) of bromine in 100 ml of methylene chloride was added dropwise to a solution of 18.1 g (50 mmol) of this chalconecarboxylic acid in 100 ml of methylene chloride at −5° to 0° C. The mixture was stirred for 1 h and then the solvent was removed under reduced pressure.

The residue was taken up in 85 ml of methanol and added to the 29.2 g of a 30% strength methanolic sodium methanolate solution. The reaction mixture was stirred at 65° C. for 3 h, allowed to cool to 25° C. and acidified with 9 ml of concentrated hydrochloric acid. The mixture was again stirred at 65° C. for 3 h and then left to stand at room temperature overnight. The precipitate was filtered off with suction and dried.

To purify the crude product it was dissolved in 2N sodium hydroxide solution and extracted 3x with ether. Remaining ether was driven out of the aqueous phase with nitrogen, and it was then acidified with concentrated hydrochloric acid. The crystals were filtered off with suction and dried, resulting in 10.3 g of the title compound of melting point 200°–202° C.

EXAMPLE 5

1-(4-Carbomethoxyphenyl)-4-(5,6,7,8-tetrahydro-5,5,8,8-tetramethyl-2-naphthyl)-1,4-butaredione 73.5 g (0.55 mol) of anhydrous aluminum chloride were added a little at a time to a solution of 70 g (0.55 mol) of chloropropionyl chloride in 200 ml of methylene chloride at 0° to 5° C. and then, at the same temperature, a solution of 94 g (0.5 tool) of 1,2,3, 4-tetrahydro-1,1,4,4-tetramethylnaphthalene in 200 ml of methylene chloride was added dropwise. The mixture was stirred at room temperature overnight, poured into 1 l of ice/water and extracted 3x with 300 ml of methylene chloride each time. The combined organic phases were washed with saturated sodium bicarbonate solution and water, dried over magnesium sulfate and concentrated. 138 g of 6-(3-chloropropionyl)-1,2,3, 4-tetrahydro-1,1,4,4-tetramethylnaphthalene remained as an oil. The structure was confirmed by H NMR spectroscopy.

5.6 g (0.02 tool) of 6-(3-chloropropionyl)-1,2,3,4-tetrahydro-1,1,4,4-tetramethylnaphthalene and 3.3 ml (0.024 tool) of triethylamine were stirred in 30 ml of dimethylformamide at room temperature for 1 h. Then a solution of 3.6 g (0.025 mol) of methyl 4-formylbenzoate and 1 g of 3-benzyl-5-(2-hydroxyethyl)-4-methylthiazolium chloride in 10 ml of dimethylformamide was added dropwise. The mixture was stirred for 1 h and then poured in to ice/water and extracted 2x with ethyl acetate, and the combined organic extracts were washed several times with water, dried over magnesium sulfate and concentrated. Recrystallization of the residue (6.4 g) from ethanol resulted in 3.7 g of the title compound of melting 139°–141° C.

EXAMPLE 6

1-(4-Carbomethoxyphenyl)-2-(5,6,7,8-tetrahydro-5,5,8,8-tetramethyl-2-naphthyl)ethanedione 7.9 g (33 mmol) of potassium tert-butanolate were added a little at a time to a suspension of 34.5 g (66 mmol) of 4-carbomethoxybenzyltriphenylphosphonium bromide were added in 200 ml of dry toluene at room temperature. The mixture was stirred for 10 min and then heated to reflux, and 7.5 g (33 mmol) of 5,6,7,8-tetrahydro-5,5,8,8-tetramethylnaphthalene-2-carbonyl chloride were added dropwise. After the solution had become colorless again it was allowed to cool and solids were filtered off. The filtrate was concentrated, and the remaining oil was recrystallized from methanol (11.2 g of the ylide intermediate of melting point 101°–203° C.). 3.2 g of the ylide and 3.1 g of sodium periodate were refluxed in a mixture of 40 ml of ethanol and 10 ml of water for 1 h. Saturated brine was added to the cooled reaction mixture, which was then extracted with methylene chloride. The organic phase was dried over magnesium sulfate and concentrated. The residue was triturated in n-heptane, the solids were filtered off, and the filtrate was concentrated. Recrystallization from ethanol yielded 1.5 g of the title compound of melting point 93°–96° C.

EXAMPLE 7

2-(4-Carboxyphenyl)-1-(5,6,7,8-tetrahydro-3-methoxy-5,5,8,8-tetramethyl-2-naphthyl)ethanone 14.6 g (29 mmol) of 1,2-dibromo-1-(4-cyanophenyl)-2-(5,6,7,8-tetrahydro-3-methoxy-5,5,8,8-tetramethyl-2-naphthyl)ethane, which had been obtained by bromination of (E)-4-[2-(5,6,7,8-tetrahydro-3-methoxy-5,5,8,8-tetramethyl-2-naphthyl)-1-ethenyl]benzonitrile with elemental bromine in chloroform, and 15.3 g of potassium hydroxide pellets were refluxed in 38 ml of n-butanol for 1 h. The mixture was then poured into ice/water and the mixture was acidified with 2N hydrochloric acid and extracted 3x with ether. The combined ether extracts were washed to neutrality with water, dried over sodium sulfate and concentrated. The residue, which contained n-butanol, had produced crystals after 3 days, and these were filtered off with suction and washed with a little ethanol. This resulted in 2.9 g of the title compound of melting point 164°-165° C.

EXAMPLE 8

2-(4-Carbomethoxyphenyl)-1-(5,6,7, 8-tetrahydro-5,5,8,8-tetramethyl-2-naphthyl)ethanone A solution of 4 g (16 mmol) of 5,6,7, 8-tetrahydro-5,5,8,8-tetramethylnaphthalene-2-carbonyl chloride and 4 g (16 mmol) of methyl 4-bromomethylbenzoate in 20 ml of dimethoxyethane was added dropwise to a solution or suspension of 0.56 g of bis(triphenylphosphine)palladium(II) dichloride and 2.1 g of zinc powder in 40 ml of dimethoxyethane at room temperature. The reaction mixture was then refluxed for 6 h. After cooling, solids were filtered off and the filtrate was heated with active carbon and filtered hot. The filtrate was concentrated and yielded after recrystallization 3x from methanol and finally from isopropanol 0.9 g of the title compound of melting point 103°-104° C.

EXAMPLE 9

2-(4-Carbomethoxyphenyl)-1-(5,6,7, 8-tetrahydro-4-methoxy-5,5,8,8-tetramethyl-2-naphthyl)ethanone 5,6,7,8-tetrahydro-4-methoxy-5,5,8, 8-tetramethylnaphthalene-2-carbonyl chloride:

A mixture of 20 g (86 mmol) of 1,2,3, 4-tetrahydro-5-methoxy-1,1,4,4,7-pentamethylnaphthalene, 4.9 g of sodium hydroxide, 58 ml of pyridine and 30 ml of water was heated to 95° C. Then 32.5 g of potassium permanganate were added a little at a time at this temperature. The mixture was stirred at 95° C. for 2 h and then cooled, and 6 ml of ethanol were slowly added dropwise. Next day the manganese dioxide was filtered and washed with hot 2N sodium hydroxide solution. The filtrate (2 phases) was mixed with ether, resulting in 3 phases. The middle phase was separated out, extracted 2x with petroleum ether and acidified with concentrated hydrochloric acid. The white precipitate was filtered off with suction and dried: 9.2 g of 5,6,7,8-tetrahydro-4-methoxy-5,5,8, 8-tetramethylnaphthalene-2-carboxylic acid.

5 g (19 mmol) of this were dissolved in 30 ml of toluene. 3 drops of dimethylformamide were added and then 2.9 g (23 mmol) of oxalyl chloride were slowly added dropwise. The mixture was stirred at room temperature for 30 min and then heated to 70° C. and stirred at this temperature until there was no more evolution of gas. The mixture was cooled and the solvent was removed under reduced pressure. The residue was 6.1 g of crude 5,6,7, 8-tetrahydro-4-methoxy-5,5,8.8-tetramethylnaphthalene-2-carbonyl chloride, whose structure was confirmed by H NMR.

2- (4-Carbomethoxyphenyl)-1-(5,6,7, 8-tetrahydro-4-methoxy-5,5,8,8-tetramethyl-2-naphthyl)ethanone 2.1 g of zinc powder and 0.21 g of copper(II) acetate were stirred with 7.3 ml of acetic acid at 20° C., with cooling, for 30 min. The zinc/copper couple was filtered off with suction and washed 2x with dry ether and 1x with dry dimethoxyethane. A solution of 4.5 g (16 mmol) of 5,6,7,8-tetrahydro-4-methoxy-5,5,8, 8-tetramethylnaphthalene-2-carbonyl chloride and 3.7 g (16 mmol) of methyl 4-bromomethylbenzoate in 60 ml of dimethoxyethane was added dropwise to a suspension of the zinc/copper couple prepared in this way and of 0.56 g of bis(triphenylphosphine)palladium(II) chloride in 15 ml of dimethoxyethane at room temperature. The mixture was stirred for 75 min and then filtered through Celite, and the filtrate was concentrated. Three recrystallizations of the residue from methanol yielded 2.0 g of the title compound of melting point 143°-144° C.

EXAMPLE 10

1-(4-Carbomethoxyphenyl)-2-(5,6,7, 8-tetrahydro-5,5,8,8-tetramethyl-2-naphthyl)ethanone 6-Bromomethyl-1,2,3,4-tetrahydro-1,1,4, 4-tetramethylnaphthalene:

A mixture of 117.5 g (0.66 mol) of N-bromosuccinimide and 2 g of 2,2'-azodiisobutyronitrile was added a little at a time to a solution of 121 g (0.6 mol) of 1,2,3,4-tetrahydro-1,1,4,4,6-pentamethylnaphthalene and 1 spatula-tip of 2,2'-azodiisobutyronitrile in 1 l of 1,2-dichloroethane at 80° C. After the addition was complete, the mixture was stirred at about 80° C. for 75 min. It was then allowed to cool, the solvent was removed under reduced pressure, and the residue was triturated with n-heptane. The precipitate was filtered off, and the filtrate was concentrated. The residue was distilled, resulting in 109 g of 6-bromomethyl-1,2,3, 4-tetrahydro-1,1,4,4-tetramethylnaphthalene of boiling point 122°-124° C. (0.3 mbar).

1-(4-Carbomethoxyphenyl)-2-(5,6,7, 8-tetrahydro-5,5,8,8-tetramethyl-2-naphthyl)ethanone In a similar manner to Example 9, 0.3 g of the title compound of melting point 96°-97° C. was obtained from 10 g (50 mmol) of monomethyl terephthalate and 14 g (50 mmol) of 6-bromomethyl-1,2,3,4-tetrahydro-1,1,4,4-tetramethylnaphthalene.

EXAMPLE 11

2-(4-Carboxyphenyl)-1-(5,6,7, 8-tetrahydro-5,5,8,8-tetramethyl-2-naphthyl)ethanone 65.4 g (0.3 mol) of 5,6,7,8-tetrahydro-5,5,8, 8-tetramethyl-2-naphthaldehyde, 56 g (0.38 mol) of ethyl orthoformate and 0.3 g of 4-toluenesulfonic acid in 75 ml of absolute ethanol were stirred at room temperature for 16 h. Then 7.6 g of anhydrous sodium carbonate were added, the mixture was stirred for about 15 min, the solids were filtered off, and the filtrate was concentrated. 92 g of diethyl acetal remained. 73.5 g (0.25 mol) of this diethyl acetal and 42.2 g (0.25 mol) of triethyl phosphite were dissolved in 240 ml of dry methylene chloride and, at −20° C. under nitrogen, 38 g (0.265 mol) of boron trifluoride diethyl etherate were added dropwise. The mixture was allowed to reach room temperature overnight, then 80 ml of water were added, the phases were separated, and the organic phase was dried over sodium sulfate and concentrated. Purification by column chromatography (silica gel; n-heptane/ethyl acetate 1:0→1) resulted in 33.3 g of slightly impure diethyl 1-ethoxy-1-(5,6,7,8-tetrahydro-5,5,8, 8-tetramethyl-2-naphthyl)methylphosphonate as an oil whose structure was confirmed by H and C NMR.

28 ml (44 mmol) of a 1.6M solution of n-butyllithium in n-hexane were slowly added dropwise to a solution of 7.6 g (20 mmol) of this phosphonate in 30 ml of absolute tetrahydrofuran at −78° C. under nitrogen. The mixture was stirred for 30 min and then, likewise at −78° C., a solution of 3.3 g (20 mmol) of methyl 4-formylbenzoate in 20 ml of tetrahydrofuran was added dropwise. The mixture was allowed to warm to room temperature and was then stirred for 1 h. It was poured into water, the mixture was extracted with ether, and the ether phase was washed with water, dried over sodium sulfate and concentrated. The residue was purified by column chromatography (silica gel; n-heptane/ethyl acetate 95:5), resulting in 6.7 g of slightly impure 2-(4-carbomethoxyphenyl)-1-ethoxy-1-(5,6,7,8-tetrahydro-5,5,8,8-tetramethyl-2-naphthyl)ethene. 2 g (5 mmol) of this and 0.5 g of potassium hydroxide in a mixture of 15 ml of methanol and 10 ml of water were refluxed for 3 h. After the mixture had been cooled it was poured into water and extracted with ether. The aqueous phase was acidified with 2N hydrochloric acid, and the crude product which separated out as an oil was extracted with ether. The ether extract was concentrated, and the residue was dissolved in 16 ml of tetrahydrofuran. 4 ml of 2N hydrochloric acid were added, and the reaction mixture was refluxed for 3 h. It was allowed to cool, water was added, the phases were separated, and the organic phase was concentrated. The residue was 0.5 g of the title compound of melting point 204°–206° C., $R_F$=0.39 (TLC: silica gel; methylene chloride/methanol 9:1).

EXAMPLE 12

1-(4-Carboxyphenyl)-2-(5,6,7,8-tetrahydro-5,5,8,8-tetramethyl-2-naphthyl)ethanedione 3.9 g (10 mmol) of 1-(4-Carbomethoxyphenyl)-2-(5,6,7,8-tetrahydro-5,5,8,8-tetramethyl-2-naphthyl)ethanedione (Example 6) were refluxed in a mixture of 5 ml of concentrated sulfuric acid, 80 ml of glacial acetic acid and 40 ml of water for 8 h. The mixture was then poured into 500 ml of water, and the crystalline precipitate was filtered off with suction and washed with water until the washings were neutral. The dried crude product was recrystallized from cyclohexane, yielding 3.1 g of the title compound of melting point 148°–151° C.

We claim:

1. A compound of the formula I

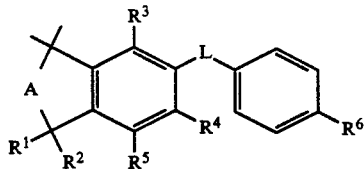

where
A is ethylene or methylene which can be substituted by methyl, hydroxyl or oxo,
L is one of the following

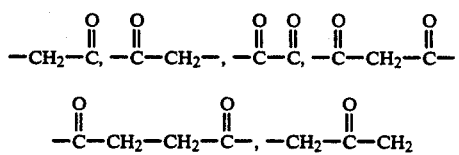

$R^1$ and $R^2$ are hydrogen or methyl,
$R^3$ is hydrogen, hydroxyl or $C_1$-$C_6$-alkoxy,
$R^4$ is hydrogen, $C_1$-$C_4$-alkyl, halogen or methoxy,
$R^5$ is hydrogen, or methoxy, and
$R^6$ is

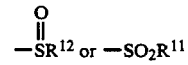

or CHR$^7$—OH
where
$R^7$ is hydrogen or $C_1$-$C_4$-alkyl,
$R^{11}$ is hydrogen, $C_1$-$C_4$-alkyl, or —OR$^{13}$ or —NR$^{14}$R$^{15}$ where R$^{13}$ is hydrogen, $C_1$-$C_8$-alkyl, which can be substituted by 1 or 2 hydroxyls, or aryls or aralkyl, each of which can be substituted in the aryl moiety by a substituent selected from the group consisting of methyl, methoxy, cyano, and halogen, and where R$^{14}$ and R$^{15}$ are hydrogen, or aralkyl or aryl which can be substituted by a substituent selected from the group consisting of methyl, methoxy, cyano, and halogen, or R$^{14}$ and R$^{15}$ form, together with the nitrogen to which they are bonded, a 5- or 6-membered saturated heterocyclic radical, or a 5- or 6- membered saturated heterocyclic radical which has an oxygen in addition to the nitrogen, and R$^{12}$ is $C_1$-$C_4$-alkyl, and the physiologically tolerated salts thereof.

2. 1-(4-Carbomethoxyphenyl)-3-(5,6,7, 8-tetrahydro-5,5,8,8,-tetramethyl-2-naphthyl)-1,3-propanedione.

3. 1-(4-Carboxyphenyl)-3-(5,6,7, 8-tetrahydro-5,5,8,8,-tetramethyl-2-naphthyl)-1,3-propanedione.

4. A process for the preparation of a deoxybenzoin of the formula I as claimed in claim 1, wherein L=—CH$_2$—CO— or —CO—CH$_2$—, which comprises reacting a phosphonic ester of the formula II

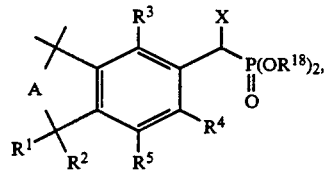

where A and R$^1$—R$^5$ have the meanings specified in claim 1, and X is —OR$^{16}$ or —NR$^{16}$R$^{17}$ where R$^{16}$, R$^{17}$ and R$^{18}$ are each $C_1$-$C_4$-alkyl, with an aldehyde of the formula III

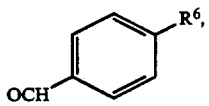

where R$^6$ has the meanings specified in claim 1, in the presence of a base, at a temperature in the range of −78° to +60° C., in a Wittig-Horner reaction, and subjecting the resulting enamine, wherein X=NR$^{16}$R$^{17}$, or enol ether, wherein X=OR$^{16}$, to acid hydrolysis 5. A process for the preparation of a 1,3-diketo compound of the formula I as claimed in claim 1, wherein L=—C(O)CH$_2$C(O)—, or of the enol tautomer thereof, which comprises
reacting a ketone of the formula VIII

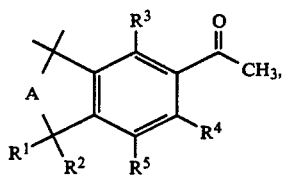

VIII where A and $R^1$—$R^5$ have the meanings specified in claim 1, with a terephthalic ester of the formula IX

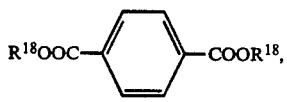

IX where $R^{18}$ is $C_1$-$C_4$-alkyl, at a temperature in the range of 20° to 140° C., in the presence of a base 6. A process for the preparation of a 1,4-diketo compound of the formula I as claimed in claim 1, wherein L=—C(O)CH$_2$CH$_2$C(O)—, which comprises reacting a chloroethyl ketone of the formula XI

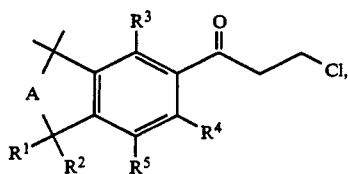

XI where A and $R^1$ to $R^5$ have the meanings specified in claim 1, with a base to give a vinyl ketone of the formula XII

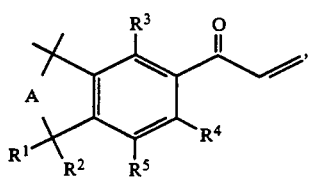

XII where A and $R^1$ have the meanings specified in claim 1, and then coupling the latter with a benzaldehyde of the formula XIII

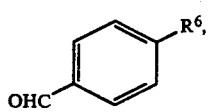

XIII where $R^6$ has the meaning specified in claim 1, in an umpolung reaction catalyzed by cyanide ions or thiazolium salts.

7. A process for the preparation of a deoxybenzoin of the formula I as claimed in claim 1, wherein L=—CH$_2$—CO— or —CO—CH$_2$—, which comprises reacting a carbonyl chloride selected from the group consisting of formula IV and V

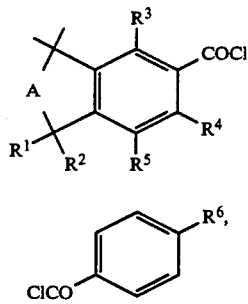

IV

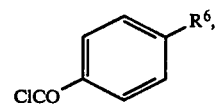

V where A and $R^1$—$R^6$ have the meanings specified in claim 1, with a benzyl halide selected from the group consisting of formula VI and VII where A and $R^1$—$R^6$ have the meanings specified in claim 1, and Y is chlorine or bromine, at a temperature in the range of 0° to 60° C., in the presence of a suitable metal, with or without the addition of catalytic amounts of a transition metal catalyst, the reaction being between either IV and VII or V and VI.

8. A process for the preparation of a 1,3-deketo compound of the formula I as claimed in claim 1, wherein L=—C(O)CH$_2$C(O)—, or of the enol tautomer thereof, which comprises subjecting a chalcone of formula X

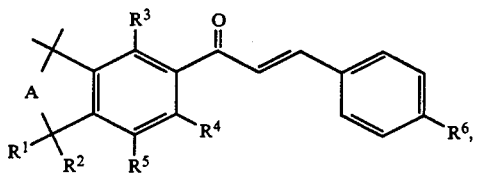

X where A and $R^1$—$R^6$ have the meanings specified in claim 1, to addition of bromine, then eliminating hydrogen bromide with a suitable base, and finally carrying out acid hydrolysis.

9. A pharmaceutical composition effective for the treatment of a dermatological disorder associated with pathological keratinization, precancerose, carcinoma, corneopathy, rheumatic disorder or arthritic disorder, comprising an effective amount of said compound according to claim 1 and a pharmaceutically acceptable auxiliary.

10. A method of treating a dermatological disorder associated with pathological keratinization, precancerose, carcinoma, corneopathy, rheumatic disorder or arthritic disorder, comprising topically administering said composition according to claim 13 to a patient in need thereof.

11. A method of treating a dermatological disorder associated with pathological keratinization, precancerose, carcinoma, corneopathy, rheumatic disorder or arthritic disorder, comprising systematically administering said composition according to claim 13 to a patient in need thereof.

* * * * *